United States Patent
Fontova Sosa et al.

(10) Patent No.: US 9,689,781 B2
(45) Date of Patent: Jun. 27, 2017

(54) SAMPLE TAKING DEVICE

(71) Applicant: Ruag Schweiz AG, Emmen (CH)

(72) Inventors: Andreu Fontova Sosa, Barcelona (ES); Enric Sarró Casanovas, Sentmenat (ES)

(73) Assignee: RUAG SCHWEIZ AG, Emmen (CH)

( * ) Notice: Subject to any disclaimer, the term of this patent is extended or adjusted under 35 U.S.C. 154(b) by 0 days.

(21) Appl. No.: 14/383,902

(22) PCT Filed: Mar. 7, 2013

(86) PCT No.: PCT/EP2013/054632
§ 371 (c)(1),
(2) Date: Sep. 9, 2014

(87) PCT Pub. No.: WO2013/132019
PCT Pub. Date: Sep. 12, 2013

(65) Prior Publication Data
US 2015/0031072 A1  Jan. 29, 2015

(30) Foreign Application Priority Data
Mar. 9, 2012  (EP) .................................... 12382086

(51) Int. Cl.
*G01N 1/14* (2006.01)
*C12M 1/26* (2006.01)
*G01N 1/20* (2006.01)

(52) U.S. Cl.
CPC ............. *G01N 1/14* (2013.01); *C12M 33/04* (2013.01); *G01N 2001/1445* (2013.01); *G01N 2001/2071* (2013.01)

(58) Field of Classification Search
CPC ..................... G01N 35/1016; G01N 2001/1418–2001/1463; C12M 33/12
(Continued)

(56) References Cited

U.S. PATENT DOCUMENTS 2,097,571 A   11/1937   Moran et al.
4,612,815 A    9/1986   Green et al.
(Continued)

FOREIGN PATENT DOCUMENTS

GB   1471865 A   4/1977

OTHER PUBLICATIONS

International Search Report and Written Opinion of the International Searching Authority Search Report Application No. PCT/EP2013/054632 issued by the European Patent Office, Rijswijk, Netherlands dated Jun. 5, 2013.
(Continued)

*Primary Examiner* — Jill Warden
*Assistant Examiner* — Matthew Krcha
(74) *Attorney, Agent, or Firm* — Peter B. Scull; Hamilton, DeSanctis & Cha LLP

(57) ABSTRACT

Sample taking device for extracting a fluid sample from a vessel comprising: a cover portion for closing the vessel such that, in use a headspace is defined between the cover portion and fluid held in the vessel, a sampling chamber comprising a sampling inlet and a sampling outlet, a cannula adapted to provide, in use, fluid communication between the fluid held in the vessel and the sampling chamber through the sampling inlet, and ports to operate the device in at least two operating conditions: a sample preparing condition in which a pressure in the headspace is greater than that of the sampling chamber such that fluid flows through the cannula towards the sampling chamber and can be retained therein, and a sample dispensing condition in which fluid retained in the sampling chamber can be delivered through the sampling outlet and fluid remaining inside the cannula can return to the vessel.

27 Claims, 4 Drawing Sheets

(58) Field of Classification Search
USPC .......................................................... 422/552
See application file for complete search history.

(56) References Cited

U.S. PATENT DOCUMENTS

| | | | |
|---|---|---|---|
| 5,353,652 A * | 10/1994 | Houck | G01N 1/10 73/864.34 |
| 5,743,960 A * | 4/1998 | Tisone | B01L 3/0265 118/305 |
| 6,213,354 B1 * | 4/2001 | Kay | A61M 5/16804 222/14 |

OTHER PUBLICATIONS

Extended European Search Report for EP 12382086.2-1521 issued by the European Patent Office, Berlin, Germany and communicated Aug. 20, 2012 with date of completion of the search on Aug. 9, 2012.

* cited by examiner

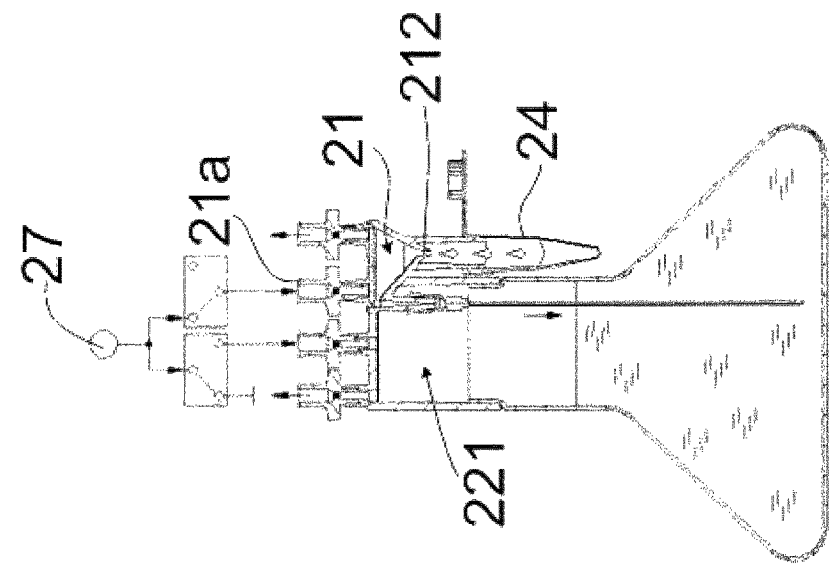
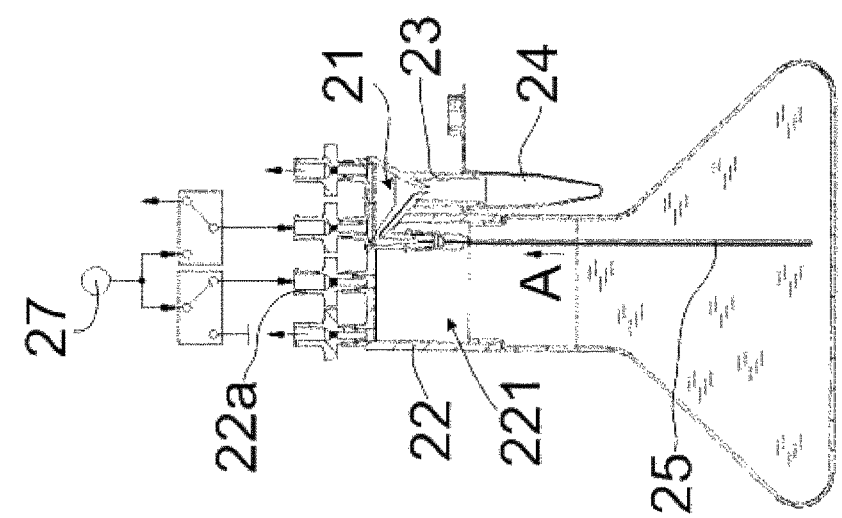
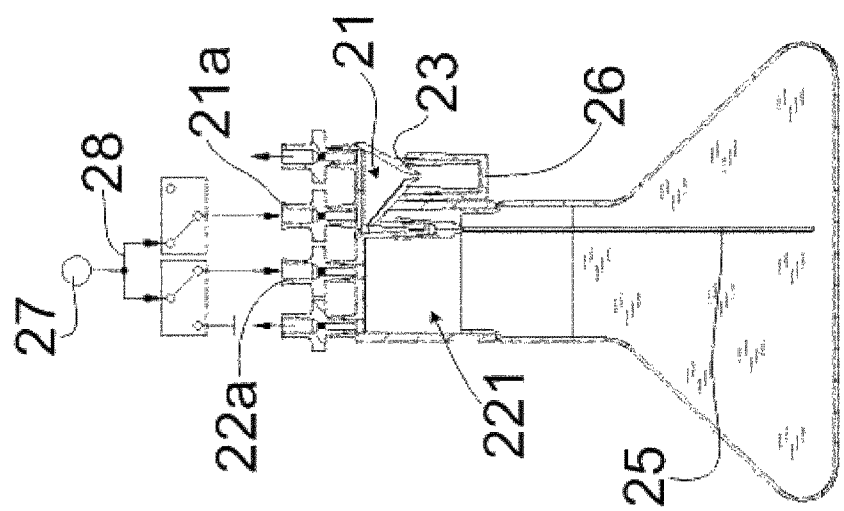

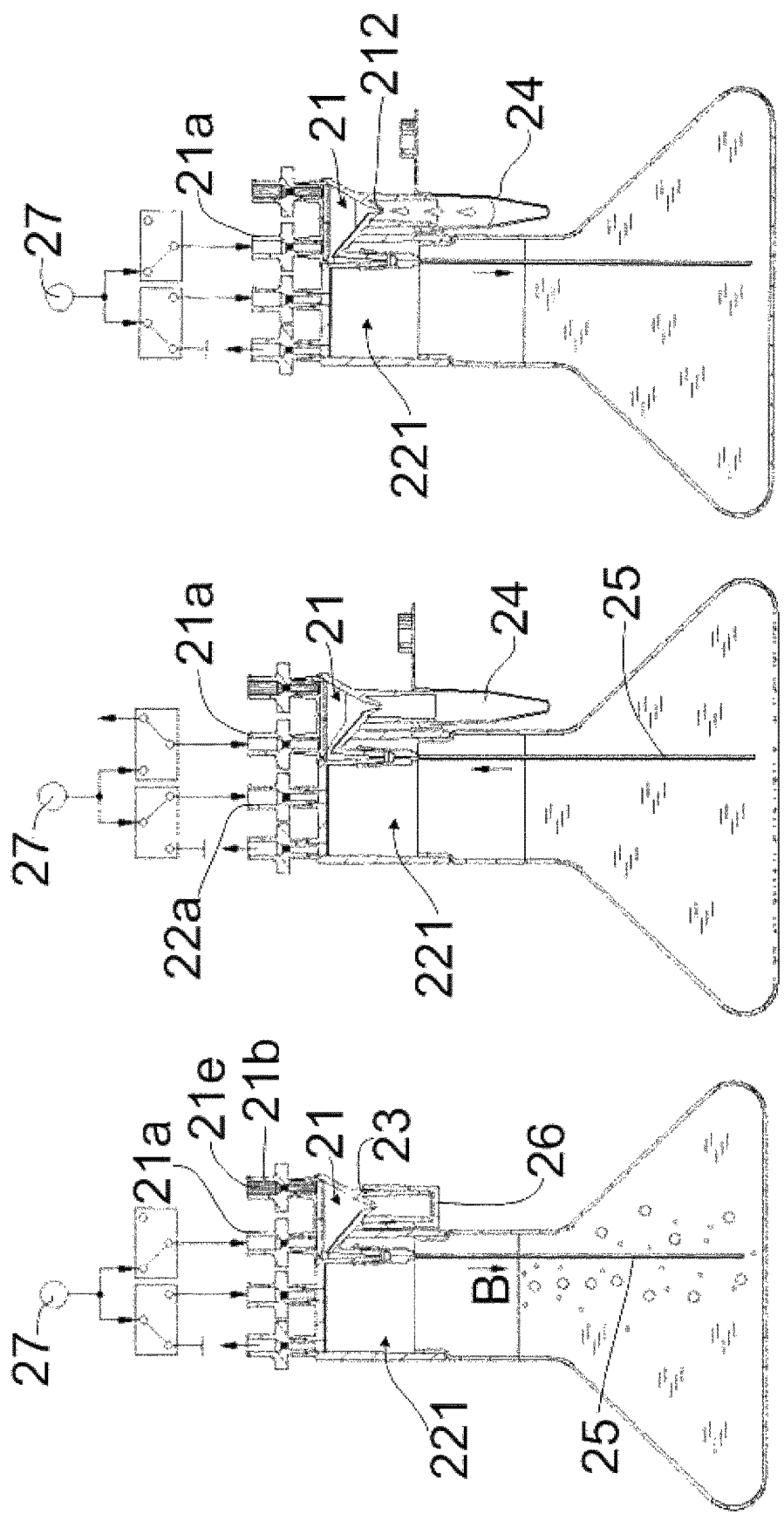

SAMPLE TAKING DEVICE

The invention relates to sample taking devices, especially sample taking devices for extracting a fluid sample from a vessel, especially from a bioreactor.

The invention further relates to a method for extracting a fluid sample from a vessel.

BACKGROUND ART

It is known that biological processes require continuous measurements of process variables. It is further known that when these biological processes are exposed to the external environment they may face the risk of contamination by viruses, micro-organisms, and/or chemicals.

Usual biological processes involve bioreactors where cells are cultured. Normally, the bioreactors are previously sterilized. For small volume reactors, the entire reactor system can be placed in an autoclave and completely sterilized. But, in many cases, these processes do not allow an easy in-situ analysis of the culture. Instead, samples must be physically extracted from the vessel/reactor and examined and manipulated outside the vessel, thereby exposing the entire culture to the external environment and to the possibility of contamination. Therefore, maintaining a contamination-free environment and/or being able to take multiple sterile samples from a reactor is a must.

Typically, extraction of samples within a system having a sterile environment that, during operation, must not come into direct communication with a non-sterile environment, has been carried out manually by connecting a pre-sterilized sample container to an outlet of the reactor/vessel containing the culture of interest. For example, a pre-sterilized container sealed by one-time use septa may be placed in communication with the vessel by puncturing the septa with a needle in fluid communication with the vessel. The needle may then inject the sample into a pre-sterilized container, the container may then be removed from the system and the sample may be analysed. This kind of sample extractions is carried out with sterilized disposable materials.

Thus, there still exists a need to provide a sample taking device by which a sample can be easily obtained, ensuring the sterility of the sample and the sterility of the fluid remaining in the vessel and which can be used repeatedly, for example for taking several samples from the same vessel over time.

SUMMARY

In a first aspect, a sample taking device for extracting a fluid sample from a vessel is provided. The sample taking device comprises:
- a cover portion suitable for closing the vessel such that, in use, a headspace is defined between the cover portion and a fluid held in the vessel,
- a sampling chamber comprising a sampling inlet and a sampling outlet,
- a cannula adapted to provide, in use, fluid communication between the fluid held in the vessel and the sampling chamber through the sampling inlet, and
- ports to operate the device in at least two operating conditions:
  a) a sample preparing condition in which a pressure in the headspace is greater than that of the sampling chamber such that fluid flows through the cannula towards the sampling chamber and can be retained therein, and
  b) a sample dispensing condition in which fluid retained in the sampling chamber can be delivered through the sampling outlet and fluid remaining inside the cannula can return to the vessel.

As used herein, "in fluid communication" refers to a relationship between two enclosures or volumes by which fluid can be permitted to flow from one volume to the other and vice-versa.

According to this aspect, the presence of two enclosures (sampling chamber and headspace above the fluid held in the vessel) in fluid communication allows the flow of fluid to be governed by the pressure inside each enclosure. This way, by controlling the pressure inside at least one of the enclosures a sample can be provided inside the sampling chamber and then delivered through the sampling outlet in quite an easy manner. Furthermore, there is no risk of contamination of the fluid and the device can be used for taking several samples out of the same vessel, as no contact of the fluid inside the vessel with the environment takes place. It is also a cost-effective solution.

In some embodiments, in the sample dispensing condition a pressure in the sampling chamber may be greater than that of the headspace. This way, on one hand the flow of fluid between the vessel and the sampling chamber may be interrupted and on the other hand, the fluid retained in the sampling chamber can be delivered through the sampling outlet. Delivery of the sample once the flow of fluid between the vessel and the sampling chamber is interrupted avoids contamination of the fluid which may remain in the vessel.

In some embodiments, a bottom portion of the sampling chamber may comprise a funnel shape and the sampling outlet may be arranged in a bottom of the funnel shape such that, in the sample preparing condition, the fluid reaching the sampling chamber can be retained therein and in the sample dispensing condition the fluid can be delivered in drops. This ensures that at delivery of a sample, the continuity solution can be broken thus avoiding contamination of any fraction of fluid which may remain inside the device.

In some of these embodiments, the sampling chamber may be designed such that a section of the sampling outlet depends on a maximum height of the fluid allowed therein, on fluid density and on fluid surface tension. These parameters may be set such that the force exerted by the mass of fluid retained on top of the sampling outlet does not break the surface tension force and no drops are yet formed. This way, the fluid may be retained inside the sampling chamber. This ensures that no drops are formed during the sample preparing condition, before the user decides to operate the device in the sample dispensing condition.

In some embodiments, the sampling outlet may be surrounded by a peripheral wall extending outwards from the sampling chamber. Such a wall may be arranged at a distance from the sampling outlet such that drops delivered by the sampling outlet do not touch an inner side of the peripheral wall. The fact that the wall is arranged so that the drops do not touch its inner side ensures that no continuity solution will be formed along such an inner side of the wall in the sample dispensing condition. This avoids contamination risks of a portion of fluid that may remain inside the sampling chamber. Such a peripheral wall may further constitute a dispensing tube.

Furthermore, provided the peripheral wall (dispensing tube) is sufficiently long, it may prevent access of any strange body (and thus contamination) to the sampling outlet.

In some of these embodiments, an outer surface of the peripheral wall may comprise an end portion provided with longitudinal grooves to allow air exhaust. This way, a vial or any type of container for receiving a sample, may be connected to the peripheral wall avoiding air tight closure of the vial with the wall thus allowing the drops to fall into the vial or container for receiving the sample.

In some embodiments, the ports to operate the device in at least two operating conditions may comprise ports for connection to a gas supply system in at least one of the sampling chamber or the cover portion. This is one possibility to regulate the pressure inside the sampling chamber and/or the headspace.

In some embodiments, the ports to operate the device in at least two operating conditions may further allow the device to be operated in an aeration condition in which a pressure difference between the sampling chamber and the headspace may be such that no fluid circulates from the vessel towards the sampling chamber. This is of special interest in those cases in which the fluid held in the vessel requires aeration and e.g. for drying the device in between different sample takings.

In another aspect a bioreactor comprising a culture vessel and a sample taking device substantially as hereinbefore described is provided. The cover portion of the sample taking device may be mounted on the culture vessel and the cannula may be adapted to provide, in use, fluid communication between the fluid held in the culture vessel and the sampling chamber through the sampling inlet.

Another aspect provides a method for extracting a fluid sample from a vessel. The method may comprise causing a depression inside a sampling chamber with respect to a headspace provided above the fluid held in the vessel such that fluid held in the vessel can flow towards the sampling chamber and can be retained therein, the cannula may be adapted to provide, in use, fluid communication between the fluid held in the vessel and the sampling chamber through the sampling inlet.

In some embodiments, the method may further comprise increasing the pressure inside the sampling chamber with respect to that of the headspace such that the fluid retained in the sampling chamber can be delivered in drops through a sampling outlet arranged at a bottom of the sampling chamber.

In some embodiments, the method may be carried out in a vessel having a sample taking device substantially as hereinbefore described.

With a method substantially as hereinbefore described, multiple sterile samples of a fluid held in the vessel may be obtained.

Additional objects, advantages and features of embodiments of the invention will become apparent to those skilled in the art upon examination of the description, or may be learned by practice of the invention.

BRIEF DESCRIPTION OF THE DRAWINGS

Particular embodiments of the present invention will be described in the following by way of non-limiting examples, with reference to the appended drawings, in which:

FIG. 1b shows a cross-sectional view of FIG. 1a;

FIGS. 2a, 2b and 2c show three different operating conditions of FIG. 1b;

FIGS. 3a, 3b and 3c show a cross-sectional view of a vessel comprising a sample taking device according to a second embodiment in three different operating conditions.

DETAILED DESCRIPTION

Figure 1A:
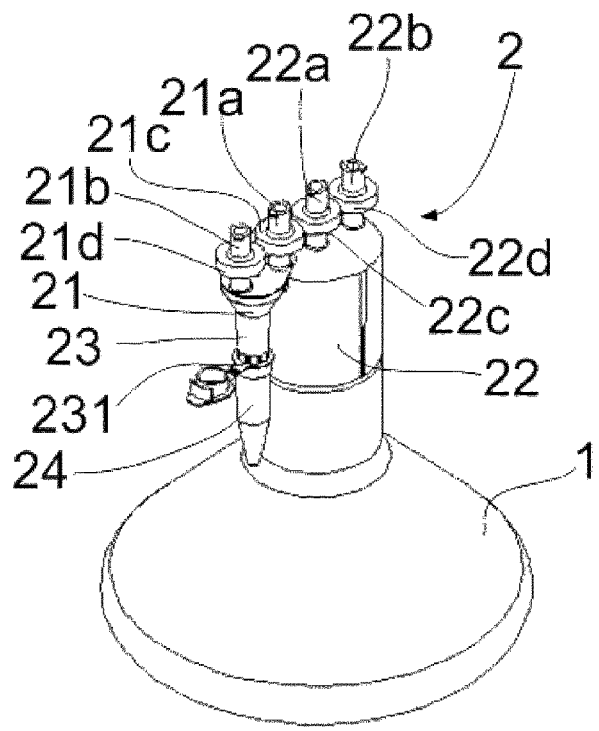
FIG. 1a shows a perspective view of a vessel comprising a sample taking device according to a first embodiment.

FIG. 1a shows a perspective view of a vessel 1 comprising a sample taking device 2 according to a first embodiment. The sample taking device 2 may comprise a cover portion 22 closing the vessel 1. The cover portion 22 may comprise an intake port 22a and an outlet port 22b. Each port 22a, 22b may comprise an aeration filter 22c, 22d. The sample taking device 2 may further comprise a sampling chamber (see FIG. 1b). The sampling chamber may comprise an intake port 21a and an outlet port 21b. Each port 21a, 21b may comprise an aeration filter 21c, 21d.

In some cases, all aeration filters 21c, 21d, 22c, 22d may have substantially similar properties. As used herein "substantially similar properties" means that they allow substantially the same air/gas flow to pass through them. In some cases at least the two aeration filters 21c, 22c arranged at the two intake ports 21a, 22a respectively may be substantially the same and the two aeration filters 21d, 22d arranged at the two outlet ports 21b, 22b may be substantially the same. It should be understood that at least the incoming air/gas flows and the outgoing air/gas flows should be substantially the same in order to facilitate operation by the user and avoid undesired imbalances of pressure.

According to FIG. 1a, the sampling chamber may be connected to a dispensing tube 23. Such a dispensing tube 23 may comprise an end portion provided with longitudinal grooves 231. An Eppendorf 24 or any other type of vial or container for receiving a sample may be placed underneath the dispensing tube 23. In the case of an Eppendorf 24 or vial, the longitudinal grooves 231 may thus avoid air tight sealing of the container with the dispensing tube 23.

Figure 1B:
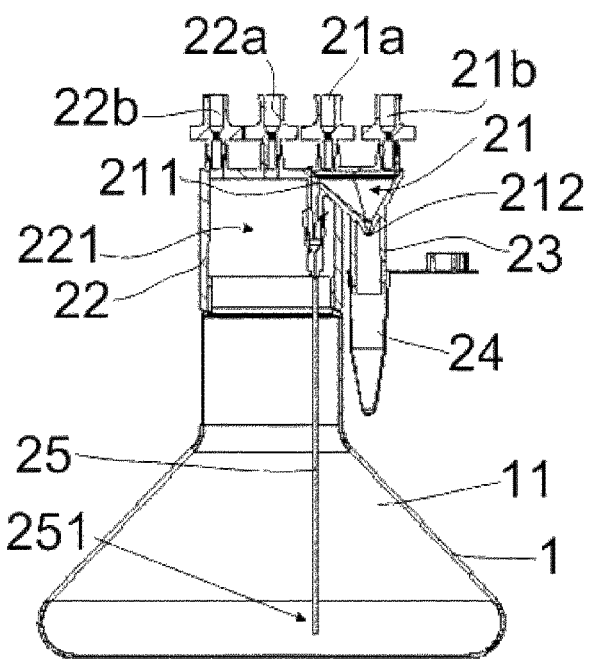

FIG. 1b shows a cross-sectional view of FIG. 1a. The sampling chamber 21 may comprise an inlet 211 and an outlet 212. The cover portion 22 may close a vessel thus defining a headspace 221 between fluid 11 held in the vessel 1 and the cover portion 22. The device may further comprise a cannula 25 arranged with one end 251 submerged in the fluid 11 held in the vessel and with the other end in communication with the sampling inlet 211. Such a cannula 25 may provide fluid communication between the fluid 11 held in the vessel 1 and the sampling chamber 21 through the sampling inlet 211. Furthermore, the sampling chamber 21 may comprise a funnel shape and the sampling outlet 212 may be arranged at the bottom of such a funnel shape.

FIGS. 2a, 2b and 2c show three different operating conditions of the embodiment of FIGS. 1a and 1b. FIG. 2a shows the device in an aeration condition, FIG. 2b in a sample preparing condition and FIG. 2c in a sample dispensing condition. A gas/air supply system 27 may be connectable to any of the intake ports 21a, 22a alternately or at the same time depending on the operating condition. In order to ensure the same pressure reaches intake ports 21a, 22a, a connector 28 having e.g. an inverted "Y" shape may be used. It should be understood that in other implementations, other ways to supply air/gas to the intake ports may be foreseen.

As shown in FIG. 2a, a closing element e.g. a cap 26 may be arranged at an end portion of the dispensing tube 23 and the gas/air supply system 27 may be connected simultaneously to both intake ports 21a and 22a through the connector 28. This way, a pressure inside the headspace 221 may be substantially similar to that inside the sampling chamber 21.

For example, and with the assumption that atmospheric pressure is equal to zero, considering an incoming pressure P, the pressure inside each enclosure (headspace 221 and sampling chamber 21) may be P/2. This way, no fluid flows through the cannula 25 from one enclosure to the other. Furthermore, since the pressure inside these two enclosures is substantially the same, there will be no air flow circulating through the cannula thus avoiding accidental bubbling of the fluid held in the vessel. In other implementations, other closing elements such as a stopper, a plug, a top, a lid or similar may be used.

As shown in FIG. 2b, the cap 26 may be removed and an Eppendorf 24 may be arranged at the end portion of the dispensing tube 23. The gas/air supply system 27 may now only be connected to the intake port 22a, provided in the cover portion 22, i.e. air may only be supplied to the headspace 221. The pressure inside the headspace 221 may thus be increased with respect to that inside the sampling chamber 21 and fluid may flow (see arrow A) from the vessel towards the sampling chamber 21 via the cannula 25.

As shown in FIG. 2c, the gas/air supply system 27 may now only be connected to intake port 21a provided in the sampling chamber 21. The pressure inside the sampling chamber 21 may thus be increased with respect to that inside the headspace 221 and the fluid retained in the sampling chamber 21 may thus be delivered through the sampling outlet 212. Furthermore, with such a pressure arrangement the flow of fluid from the vessel towards the sampling chamber may be interrupted. This way, contamination of the fluid which may remain inside the vessel is avoided.

FIGS. 3a, 3b and 3b show a cross-sectional view of a vessel comprising a sample taking device according to a second embodiment in three different operating conditions. FIG. 3a shows the device in an aeration condition, FIG. 3b in a sample preparing condition and FIG. 3c in a sample dispensing condition. The same reference numbers will be used for matching parts. The example of FIGS. 3a-3c differs from that of FIGS. 2a-2c in that the outlet port 21b provided in the sampling chamber may be removed. Alternatively a plug 21e or any other closure may be used for closing the outlet port 21b.

As shown in FIG. 3a, a cap 26 may be arranged at an end portion of the dispensing tube 23 and the gas/air supply system 27 may only be connected to the intake port 21a. The air inflow may now enter the sampling chamber 21 only and, because the pressure inside the headspace 221 may be lower than that inside the sampling chamber 21, the air inflow may also circulate through the cannula 25 (see arrow B) towards the fluid held in the vessel. Such an air inflow may cause the fluid held in the vessel to start bubbling. Such a bubbling may provide aeration of the fluid held in the vessel and it may also dry the cannula 25 in between different sample takings.

As shown in FIG. 3b, the cap 26 may be removed and an Eppendorf 24 may be arranged at the end portion of the dispensing tube 23. The gas/air supply system 27 may now be connected to the intake port 22a and it may be disconnected from the intake port 21a. This way, and similarly to what was explained in connection with FIG. 2b, the pressure inside the headspace 221 may be increased with respect to that inside the sampling chamber 21 and the fluid may flow (see arrow A) from the vessel towards the sampling chamber 21 via the cannula 25 and retained therein.

As shown in FIG. 3c and similar to what was explained in connection with FIG. 2c, the gas/air supply system 27 may now again be connected to intake port 21a only. The pressure inside the sampling chamber 21 may thus be increased with respect to that inside the headspace 221 and the fluid retained in the sampling chamber 21 may be delivered through the sampling outlet 212 into the Eppendorf 24.

Figure 4A:
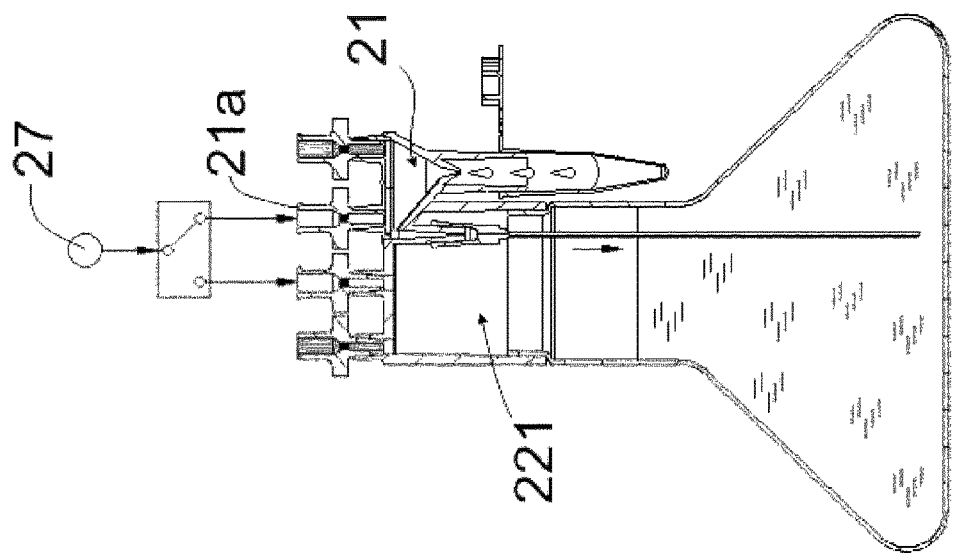
FIGS. 4a and 4b show a cross-sectional view of a vessel comprising a sample taking device according to a third embodiment in two different operating conditions.
Figure 4B:
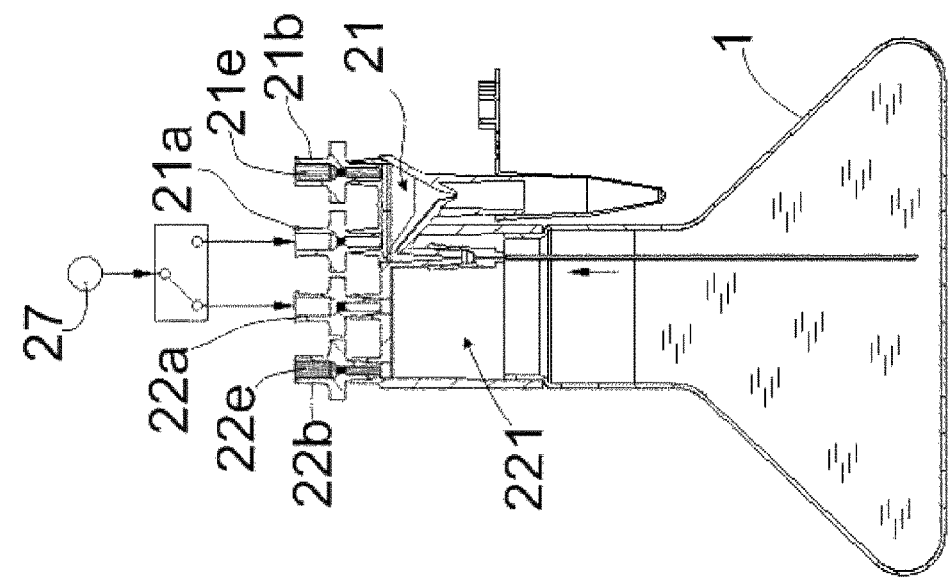

FIGS. 4a and 4b show a cross-sectional view of a vessel comprising a sample taking device according to a third embodiment in two different operating conditions. FIG. 4a shows the device in a sample preparing condition and FIG. 4b in a sample dispensing condition. The same reference numbers will be used for matching parts. The example of FIGS. 4a and 4b differs from that of FIGS. 2a-2c and 3a-3c in that both outlet ports 21b, 22b may be removed. In the example, two plugs 21e and 22e may be used for respectively closing them.

FIG. 4a shows the device in a sample preparing condition and FIG. 4b in a sample dispensing condition.

As shown in FIG. 4a, the gas supply 27 may be connected to the intake port 22a. The pressure inside the headspace 221 may thus be increased with respect to the pressure inside the sampling chamber 21 which may result in fluid circulating from the vessel 1 towards the funnel shaped sampling chamber 21. Such a fluid may be retained therein.

As shown in FIG. 4b, the gas supply 27 may now be connected to the intake port 21a provided in the sampling chamber 21 thus increasing a pressure inside the sampling chamber 21. The pressure increment may be such that drops of fluid retained in the sampling chamber 21 may start to fall out of the sampling outlet 212.

It should be noted that in all cases, in the sample dispensing condition, i.e. when the fluid retained in the sampling chamber is delivered, the pressure may be regulated so that the fluid may flow in drops or as a stream. The user may thus be able to regulate whether the fluid falls in drops or as a stream into the container for receiving a sample. This way, by controlling the pressure inside the sampling chamber, the continuity solution may be broken thus avoiding contamination of a portion of fluid which may remain inside the sampling chamber. This way, multiple sterile samples may be obtained without contamination of the fluid inside the vessel.

It should be understood that in all cases, the retention of the fluid inside the sampling chamber may depend on the dimensions of the sampling chamber and on the amount of fluid retained therein, especially on the height of the fluid received in the sampling chamber, the size of the sampling outlet, and inherent properties of the fluid such as surface tension and density. Particularly, the weight of the fluid immediately held on top of the sampling outlet should be lower than the surface tension of the fluid in order to avoid formation of drops before deciding to operate the device in the sample dispensing condition.

In addition, an inner diameter of the dispensing tube may be related with a diameter of the drops formed at the sampling outlet. In all cases, the inner diameter of the dispensing tube should be big enough to ensure that the drops delivered by the sampling outlet do not touch the inner walls of the dispensing tube. Formation of continuity solutions along such inner walls may thus be avoided.

In some embodiments, a plane containing an edge of the orifice where the drop is formed i.e. the sampling outlet, may have a certain angle with respect to a vertical plane. This favours drop formation preventing undesired sideways spread of the fluid e.g. by capillary action.

An explanation of the relations between some of the geometrical parameters of the device, and how some of these parameters can be selected, is given in the following.

In an embodiment of the device, with a sampling chamber having a sampling outlet radius ($r_o$) of 0.25 mm, some tests were made using pure water at 20° C.

The maximum height of the fluid that may be retained in the sampling chamber without leaking through the sampling outlet, when the pressure in the sampling chamber is the atmospheric pressure, may be determined in accordance with the following equation:

$$h < \frac{k \cdot 2 \cdot \gamma}{\rho \cdot g \cdot r_o}$$

wherein:

k×γ is an experimentally obtained value (68.8×10$^{-3}$ N/m) which features the surface tension of a drop of water at 20° C. which is hanging in equilibrium state from the sampling outlet ($r_o$=0.25 mm);

ρ is the density of water (1000 kg/m$^3$);

g is the acceleration of gravity (9.81 m/s$^2$).

As a result, h should be lower than about 56 mm to avoid undesired sample delivery during e.g. the sample preparing condition. The device can be dimensioned and operated accordingly.

Further, assuming the shape of a drop as substantially spherical, the radius of a drop may be determined in accordance with the following equation:

$$r_g = \left( \frac{3 \cdot k \cdot r_o \cdot \gamma}{\rho \cdot 2 \cdot g} \right)^{1/3}$$

According to this formula, the radius of the drop is about 1.38 mm. As a consequence an inner section of the dispensing tube surrounding the sampling outlet should be bigger than at least 2.76 mm in order to avoid contact of the drops with an inner wall of the dispensing tube.

A correction factor of about 0.5 may preferably be applied, as viscosity of the fluid, capillarity and imperfections of the geometry have not been considered in above calculations.

A sample taking device substantially as hereinbefore described may be configured such that samples may be obtained from a fluid held inside a closed system, such as a bioreactor. As used herein, the term "closed" refers to a system having a sterile environment that, during operation, does not come into direct communication with a non-sterile environment.

In some embodiments, a simple taking device substantially as hereinbefore described and a vessel (or bioreactor) may be made in one piece.

In some embodiments, at least the two intake ports may allow a substantially similar air flow to pass through them. In some embodiments, the two outlet ports may further allow a substantially similar air flow. In others, each intake and outlet ports may comprise a filter.

In some embodiments, a cleaning port may further be provided in a sample taking device substantially as hereinbefore described. Such a cleaning port may be arranged in the sampling chamber. This way, injection of a cleaning agent may be easily carried out without having to dismantle the device e.g. in between different sample takings.

In some embodiments the sampling outlet may comprise a non-return valve, e.g. a valve made of silicone, with which the flow of fluid retained in the sampling chamber may be controlled. In alternative embodiments, the sampling outlet may be closed by a tap and the flow of fluid retained in the sampling chamber will be controlled by the tap. Other ways for controlling the delivery of the fluid retained in the sampling chamber may be foreseen. Furthermore, a drainage may be arranged at the sampling chamber in order to return to the vessel fluid that surpasses a desired height inside the sampling chamber.

In some embodiments, a monitoring system with e.g. an alarm may be provided to control pressure balance/imbalance between the headspace and the sampling chamber. This way, in case the user fails to close an air intake port in time, the system can automatically shut the air flow and avoid the beginning of a dispensing condition when it is not desired e.g. when the sample receiving container is not arranged under the sampling outlet. An automatic closing mechanism may also be foreseen.

Although only a number of particular embodiments and examples of the invention have been disclosed herein, it will be understood by those skilled in the art that other alternative embodiments and/or uses of the invention and obvious modifications and equivalents thereof are possible. Furthermore, the present invention covers all possible combinations of the particular embodiments described. Thus, the scope of the present invention should not be limited by particular embodiments, but should be determined only by a fair reading of the claims that follow.

The invention claimed is:

1. A sample taking device for extracting a fluid sample from a vessel comprising:
    a cover portion suitable for closing the vessel such that, in use, a headspace is defined between the cover portion and a fluid held in the vessel,
    a sampling chamber comprising a sampling inlet and a sampling outlet,
    a cannula configured to provide, in use, fluid communication between the fluid held in the vessel and the sampling chamber through the sampling inlet, and
    ports configured to operate the device in at least two operating conditions:
    a) a sample preparing condition in which a pressure in the headspace is greater than that of the sampling chamber such that fluid flows through the cannula towards the sampling chamber and can be retained therein, and
    b) a sample dispensing condition in which fluid retained in the sampling chamber can be delivered through the sampling outlet and fluid remaining inside the cannula can return to the vessel;
    the ports comprising at least one connector configured for connection to a gas supply system operable to supply gas at a pressure greater than atmospheric pressure, the ports being configured to operate the device in at least the two operating conditions comprise a first intake port arranged in the cover portion and configured for connection to the gas supply system to increase to pressure inside the headspace of the vessel during the sample preparing operating condition, and a second intake port arranged in the sampling chamber and configured for connection to the gas supply system to increase the pressure inside the sampling chamber during the sample dispensing operating condition, wherein a part of the sampling chamber is mounted against and in contact with the cover portion of the vessel such that the sampling chamber is in fluid communication with the vessel.

2. A sample taking device of claim 1, wherein in the sample dispensing condition a pressure in the sampling chamber is greater than that of the headspace.

3. A sample taking device of claim 1, wherein a bottom portion of the sampling chamber comprises a funnel shape and the sampling outlet is arranged in a bottom of the funnel shape such that, in the sample preparing condition, the fluid reaching the sampling chamber can be retained therein and in the sample dispensing condition the fluid can be delivered in drops.

4. A sample taking device of claim 3, wherein the sampling chamber is configured so that a section of the sampling outlet depends on a maximum height of the fluid allowed therein, on fluid density and on fluid surface tension.

5. A sample taking device according of claim 1, wherein the sampling outlet is surrounded by a peripheral wall extending outwards from the sampling chamber, the wall being arranged at a distance from the sampling outlet such that drops delivered by the sampling outlet do not touch an inner side of the wall.

6. A sample taking device of claim 5, wherein an outer surface of the peripheral wall comprises an end portion provided with longitudinal grooves to allow air exhaust.

7. A sample taking device of claim 1, wherein the ports configured to operate the device in at least two operating conditions further comprises an outlet port arranged in the sampling chamber.

8. A sample taking device of claim 7, wherein the ports configured to operate the device in at least two operating conditions further allow the device to be operated in an aeration condition in which a pressure difference between the sampling chamber and the headspace is such that no fluid circulates from the vessel towards the sampling chamber.

9. A sample taking device of claim 8, wherein in the aeration condition a pressure in the headspace is substantially the same as that of the sampling chamber.

10. A method for extracting a fluid sample from a vessel having a sample taking device according to claim 1, comprising
providing the sample taking device of claim 1;
causing a depression inside the sampling chamber with respect to the headspace such that the fluid held in the vessel can flow towards the sampling chamber and can be retained therein, and
increasing the gas pressure inside the sampling chamber above the fluid with respect to the gas pressure of the headspace above the fluid such that the fluid retained in the sampling chamber can be delivered in drops through the sampling outlet.

11. The sample device of claim 1, wherein the sampling chamber and the cover portion of the vessel form an integral part.

12. The sample device of claim 1, wherein the cannula is arranged inside the vessel, one extremity of the cannula being immersed in the fluid held in the vessel, the other extremity of the cannula being located below the cover portion of the vessel.

13. The sample device of claim 1, wherein the integral part of the cannula is straight.

14. A bioreactor comprising a culture vessel and a sample taking device for extracting a fluid sample from the culture vessel comprising:
a cover portion mounted on and closing the culture vessel such that, in use, a headspace is defined between the cover portion and a fluid held in the culture vessel,
a sampling housing containing a sampling chamber comprising a sampling inlet and a sampling outlet,
a cannula adapted to provide, in use, fluid communication between the fluid held in the culture vessel and the sampling chamber through the sampling inlet, and
ports configured to operate the device in at least two operating conditions:
a sample preparing condition in which a pressure in the headspace is greater than that of the sampling chamber such that fluid flows through the cannula towards the sampling chamber and can be retained therein, and
a sample dispensing condition in which fluid retained in the sampling chamber can be delivered through the sampling outlet and fluid remaining inside the cannula can return to the culture vessel;
wherein the ports comprise at least one connector configured for connection to a gas supply system operable to supply gas at a pressure greater than atmospheric pressure, the ports being configured to operate the device in the at least two operating conditions comprise a first intake port arranged in the cover portion and configured for connection to the gas supply system to increase the pressure inside the headspace of the culture vessel during the sample preparing operating condition, and a second intake port arranged in the sampling chamber and configured for connection to the gas supply system to increase the pressure inside the sampling chamber during the sample dispensing operating condition wherein a part the sampling chamber is mounted against and in contact with the cover portion of the vessel such that the sampling chamber is in fluid communication with the vessel.

15. The bioreactor of claim 14, wherein the sampling chamber and the cover portion of the culture vessel form an integral part.

16. The bioreactor of claim 14, wherein the cannula is arranged inside the culture vessel, one extremity of the cannula being immersed in the fluid held in the culture vessel, the other extremity of the cannula being located below the cover portion of the culture vessel.

17. The bioreactor of claim 14, wherein the integral part of the cannula is straight.

18. Sample taking device for extracting a fluid sample from a vessel comprising:
a cover portion suitable for closing the vessel such that, in use, a headspace is defined between the cover portion and a fluid held in the vessel,
a sampling chamber containing a sampling inlet and a sampling outlet,
a cannula configured to provide, in use, fluid communication between the fluid held in the vessel and the sampling chamber through the sampling inlet, and
ports configured to operate the device in three operating conditions:
a. a device aeration condition in which a pressure difference between the sampling chamber and the headspace may be such that no fluid circulates from the vessel towards the sampling chamber,
b. a sample preparing condition in which a pressure in the headspace is greater than that of the sampling chamber such that fluid flows through the cannula towards the sampling chamber and can be retained therein, and
c) a sample dispensing condition in which fluid retained in the sampling chamber can be delivered through the sampling outlet and fluid remaining inside the cannula can return to the vessel;
the ports comprising at least one connector configured for connection to a gas supply system operable to supply gas at a pressure greater than atmospheric pressure, the ports comprising a first intake port arranged in the cover portion and configured for connection to the gas supply system to increase to pressure inside the headspace of the vessel during the sample preparing operating condition and a second intake port arranged in the sampling chamber and configured for connection to the gas supply system to increase the pressure inside the sampling chamber during the sample dispensing operating condition, wherein an outlet port is arranged in the cover portion and is configured to be in fluid communication with the atmosphere during the device aeration operating condition, wherein a part of the sampling chamber is mounted against and in contact with the cover portion of the vessel such that the sampling chamber is in fluid communication with the vessel.

19. The sample taking device of claim 18, wherein in the sample dispensing condition a pressure in the sampling chamber is greater than that of the headspace.

20. The sample taking device of claim 18, wherein a bottom portion of the sampling chamber comprises a funnel shape and the sampling outlet is arranged in a bottom of the funnel shape such that, in the sample preparing condition, the fluid reaching the sampling chamber can be retained therein and in the sample dispensing condition the fluid can be delivered in drops.

21. The sample taking device of claim 18, wherein the sampling chamber is designed such that a section of the sampling outlet depends on a maximum height of the fluid allowed therein, on fluid density and on fluid surface tension.

22. The sample taking device of claim 18, wherein the sampling outlet is surrounded by a peripheral wall extending outwards from the sampling chamber, the wall being arranged at a distance from the sampling outlet such that drops delivered by the sampling outlet do not touch an inner side of the wall.

23. The sample taking device of claim 18, wherein an outer surface of the peripheral wall comprises an end portion provided with longitudinal grooves to allow air exhaust.

24. The sample taking device of claim 18, wherein a part of the sampling chamber is permanently mounted against and in contact with the cover portion of the vessel such that the sampling chamber is in fluid communication with the vessel.

25. The sample device of claim 18, wherein the sampling chamber and the cover portion of the vessel form an integral part.

26. The sample device of claim 18, wherein the cannula is arranged inside the vessel, one extremity of the cannula being immersed in the fluid held in the vessel, the other extremity of the cannula being located below the cover portion of the vessel.

27. The sample device of claim 18, wherein the integral part of the cannula is straight.

* * * * *